(12) United States Patent
Chen et al.

(10) Patent No.: US 8,546,628 B2
(45) Date of Patent: Oct. 1, 2013

(54) HYDROISOMERIZATION PROCESS USING MOLECULAR SIEVE SSZ-81

(75) Inventors: Cong-Yan Chen, Alameda, CA (US); Stacey I. Zones, San Francisco, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 288 days.

(21) Appl. No.: 13/162,460

(22) Filed: Jun. 16, 2011

(65) Prior Publication Data

US 2011/0319696 A1    Dec. 29, 2011

Related U.S. Application Data

(60) Provisional application No. 61/358,803, filed on Jun. 25, 2010.

(51) Int. Cl.
| | |
|---|---|
| *C07C 5/22* | (2006.01) |
| *C10L 5/00* | (2006.01) |
| *C10G 45/04* | (2006.01) |
| *C10G 35/00* | (2006.01) |
| *C01B 33/36* | (2006.01) |
| *C01F 7/00* | (2006.01) |
| *B01J 29/87* | (2006.01) |
| *B01J 29/06* | (2006.01) |

(52) U.S. Cl.
USPC .......... 585/253; 585/12; 208/217; 208/133; 423/700; 423/701; 423/702; 502/60; 502/64

(58) Field of Classification Search
None
See application file for complete search history.

(56) References Cited

U.S. PATENT DOCUMENTS

| | | |
|---|---|---|
| 4,508,837 A | 4/1985 | Zones |
| 4,910,006 A | 3/1990 | Zones et al. |
| 5,316,753 A | 5/1994 | Nakagawa |
| 6,960,327 B2 | 11/2005 | Navrotsky et al. |
| 7,622,032 B2 | 11/2009 | Zones et al. |
| 2007/0284284 A1 | 12/2007 | Zones et al. |

FOREIGN PATENT DOCUMENTS

| | | |
|---|---|---|
| WO | 2010059297 | 5/2010 |
| WO | 2010065319 | 6/2010 |

OTHER PUBLICATIONS

PCT International Search report, PCT/US2011/040287, mailed Feb. 9, 2012.
S.I. Zones and T.V. Harris, "The Constraint Index test revisited: anomalies based upon new zeolite structure types" Microporous Mesoporous Mater. 35-36 (2000) 31-46.

*Primary Examiner* — Curtis Mayes
*Assistant Examiner* — Bijay Saha
(74) *Attorney, Agent, or Firm* — Michael D. Ross

(57) ABSTRACT

The present invention is directed to a hydroisomerization process using a new crystalline molecular sieve designated SSZ-81, which is synthesized using a structure directing agent selected from 1,5-bis(1-azonia-bicyclo[2.2.2]octane) pentane dications, 1,5-bis(1,4-diazabicyclo[2.2.2]octane) pentane dications, and mixtures thereof.

7 Claims, 2 Drawing Sheets

HYDROISOMERIZATION PROCESS USING MOLECULAR SIEVE SSZ-81

This application claims the benefit of U.S. Provisional Application No. 61/358,803 filed Jun. 25, 2010.

FIELD OF THE INVENTION

The present invention relates to new molecular sieve SSZ-81, a method for preparing SSZ-81 in a hydroxide media using a structure directing agent ("SDA") selected from 1,5-bis(1-azonia-bicyclo[2.2.2]octane)pentane dications, 1,5-bis(1,4-diazabicyclo[2.2.2]octane)pentane dications, and mixtures thereof, and a hydroisomerization process using SSZ-81.

BACKGROUND OF THE INVENTION

Molecular sieves are a class of important materials used in the chemical industry for processes such as gas stream purification and hydrocarbon conversion processes. Molecular sieves are porous solids having interconnected pores of different sizes. Molecular sieves typically have a one-, two- or three-dimensional crystalline pore structure having pores of one or more molecular dimensions that selectively adsorb molecules that can enter the pores, and exclude those molecules that are too large. The pore size, pore shape, interstitial spacing or channels, composition, crystal morphology and structure are a few characteristics of molecular sieves that determine their use in various hydrocarbon adsorption and conversion processes.

For the petroleum and petrochemical industries, the most commercially useful molecular sieves are known as zeolites. A zeolite is an aluminosilicate having an open framework structure formed from corner sharing the oxygen atoms of $[SiO_4]$ and $[AlO_4]$ tetrahedra or silica and alumina octahedra. Mobile extra framework cations reside in the pores for balancing charges along the zeolite framework. These charges are a result of substitution of a tetrahedral framework cation (e.g. $Si^{4+}$) with a trivalent or pentavalent cation. Extra framework cations counter-balance these charges preserving the electroneutrality of the framework, and these cations are exchangeable with other cations and/or protons.

Synthetic molecular sieves, particularly zeolites, are typically synthesized by mixing sources of alumina and silica in an aqueous media, often in the presence of a structure directing agent or templating agent. The structure of the molecular sieve formed is determined in part by solubility of the various sources, silica-to-alumina ratio, nature of the cation, synthesis conditions (temperature, pressure, mixing agitation), order of addition, type of templating agent, and the like.

Although many different crystalline molecular sieves have been discovered, there is a continuing need for new molecular sieves with desirable properties for gas separation and drying, hydrocarbon and chemical conversions, and other applications. New molecular sieves may contain novel internal pore architectures, providing enhanced selectivities in these processes.

SUMMARY OF THE INVENTION

The present invention is directed to a new family of molecular sieves with unique properties, referred to herein as "molecular sieve SSZ-81" or simply "SSZ-81."

In accordance with the present invention there is provided a molecular sieve having a mole ratio greater than about 10 of silicon oxide to aluminum oxide and having, after calcination, the powder X-ray diffraction (XRD) lines of Table 4.

The present invention farther includes a method for preparing a crystalline material by contacting under crystallization conditions: (1) at least one source of silicon; (2) at least one source of aluminum; (3) at least one source of an element selected from Groups 1 and 2 of the Periodic Table; (4) hydroxide ions; and (5) a structure directing agent selected from 1,5-bis(1-azonia-bicyclo[2.2.2]octane)pentane dications, 1,5-bis(1,4-diazabicyclo[2.2.2]octane)pentane dications, and mixtures thereof.

The present invention also includes a process for preparing a molecular sieve having, after calcination, the powder XRD lines of Table 4, by:

(a) preparing a reaction mixture containing: (1) at least one source of silicon; (2) a least one source of aluminum; (3) at least one source of an element selected from Groups 1 and 2 of the Periodic Table; (4) hydroxide ions; (5) a structure directing agent selected from 1,5-bis(1-azonia-bicyclo[2.2.2] octane)pentane dications, 1,5-bis(1,4-diazabicyclo[2.2.2]octane)pentane dications, and mixtures thereof; and (6) water; and (b) maintaining the reaction mixture under conditions sufficient to form crystals of the molecular sieve.

Where the molecular sieve formed is an intermediate material, the process of the present invention includes a further post-synthesis processing in order to achieve the target molecular sieve (e.g. by acid leaching in order to achieve a higher silica to alumina (Si:Al) ratio).

The present invention also provides a novel molecular sieve designated SSZ-81 having, as-synthesized and in the anhydrous state, in terms of mole ratios, as follows;

|  | Broadest | Secondary |
| --- | --- | --- |
| $SiO_2/Al_2O_3$ | 10-60 | 20-35 |
| $(Q + A)/SiO_2$ | 0.02-0.10 | 0.04-0.07 |
| $M/SiO_2$ | 0.01-1.0 | 0.02-0.04 | wherein:

(1) M is selected from the group consisting of elements from Groups 1 and 2 of the Periodic Table;

(2) Q is at least one 1,5-bis(1-azonia-bicyclo[2.2.2]octane) pentane dication structure directing agent, and Q≥0; and (3) A is at least one 1,5-bis(1,4-diazabicyclo[2.2.2]octane) pentane dication structure directing agent, and A≥0.

DETAILED DESCRIPTION OF THE INVENTION

Introduction

Figure 1:
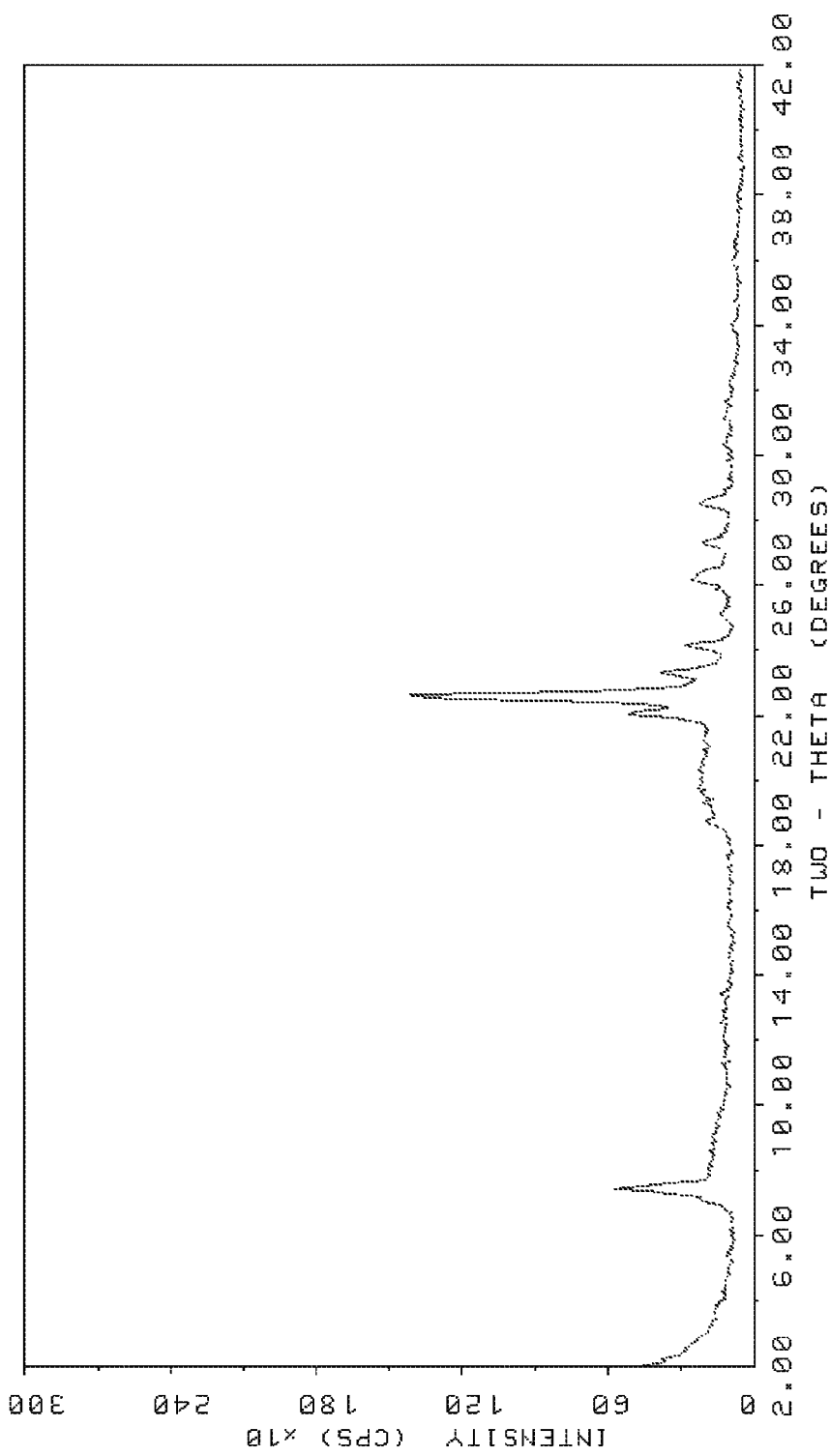
FIG. 1 shows the results of powder X-ray diffraction (XRD) analysis of the as-synthesized molecular sieve prepared in Example 1.

The term "Periodic Table" refers to the version of IUPAC Periodic Table of the Elements dated Jun. 22, 2007, and the numbering scheme for the Periodic Table Groups is as described in Chemical and Engineering News, 63(5), 27 (1985).

The term "molecular sieve" includes (a) intermediate and (b) final or target molecular sieves and molecular sieves produced by (1) direct synthesis or (2) post-crystallization treatment (secondary synthesis). Secondary synthesis techniques allow for the synthesis of a target material having a higher Si:Al ratio from an intermediate material by acid leaching or other similar dealumination methods.

Where permitted, all publications, patents and patent applications cited in this application are herein incorporated by reference in their entirety, to the extent such disclosure is not inconsistent with the present invention.

Unless otherwise specified, the recitation of a genus of elements, materials or other components, from which an individual component or mixture of components can be selected, is intended to include all possible sub-generic combinations of the listed components and mixtures thereof. Also, "include" and its variants, are intended to be non-limiting, such that recitation of items in a list is not to the exclusion of other like items that may also be useful in the materials, compositions and methods of this invention.

Reaction Mixture

The present invention is directed to a molecular sieve designated herein as "molecular sieve SSZ-81." or simply "SSZ-81."

In preparing SSZ-81, a 1,5-bis(1-azonia-bicyclo[2.2.2]octane)pentane dication, a 1,5-bis(1,4-diazabicyclo[2.2.2]octane)pentane dication, or a mixture thereof, is used as a structure directing agent ("SDA"), also known as a crystallization template. The SDAs useful for making SSZ-81 are represented by the following structures (1) and (2):

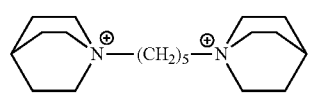

(1)

1,5-bis/1-azonia-bicyclo[2.2.2]octane)pentane dication

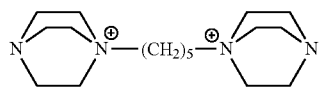

(2)

1,5-bis(1,4-diazabicyclo[2.2.2]octane)pentane dication

In general, SSZ-81 is prepared by:

(a) preparing a reaction mixture containing (1) at least one source of silicon; (2) at least one source of aluminum; (3) at least one source of an element selected from Groups 1 and 2 of the Periodic Table; (4) hydroxide ions; and (5) a structure directing agent selected from 1,5-bis(1-azonia-bicyclo[2.2.2]octane)pentane dications, 1,5-bis(1,4-diazabicyclo[2.2.2]octane)pentane dications, and mixtures thereof; and (b) maintaining the reaction mixture under conditions sufficient to form crystals of the molecular sieve.

Where the molecular sieve formed is an intermediate material, the process of the present invention includes a further step of synthesizing a target molecular sieve by post-synthesis techniques, such as acid leaching.

The composition of the reaction mixture from which the molecular sieve is formed, in terms of molar ratios, is identified in Table 1 below:

TABLE 1

| Reactants | Broad | Secondary |
|---|---|---|
| $SiO_2/Al_2O_3$ molar ratio | 20-80 | 25-35 |
| $M/SiO_2$ molar ratio | 0.05-0.30 | 0.10-0.20 |
| $(Q + A)/SiO_2$ molar ratio | 0.05-0.30 | 0.10-0.20 |
| $OH^-/SiO_2$ molar ratio | 0.20-0.60 | 0.30-0.35 |
| $H_2O/SiO_2$ molar ratio | 10-50 | 30-40 | wherein compositional variables Q, A and M are as described herein above.

Sources useful herein for silicon include fumed silica, precipitated silicates, silica hydrogel, silicic acid, colloidal silica, tetra-alkyl orthosilicates (e.g. tetraethyl orthosilicate), and silica hydroxides.

Sources useful for aluminum include oxides, hydroxides, acetates, oxalates, ammonium salts and sulfates of aluminum. Typical sources of aluminum oxide include aluminates, alumina, and aluminum compounds such as $AlCl_3$, $Al_2(SO_4)_3$, aluminum hydroxide ($Al(OH)_3$)), kaolin clays, and other zeolites. An example of the source of aluminum oxide is LZ-210 and LZ-52 zeolite (types of Y zeolites).

As described herein above, for each embodiment described herein, the reaction mixture may be formed using at least one source of an element selected from Groups 1 and 2 of the Periodic Table (referred to herein as M). In one subembodiment, the reaction mixture is formed using a source of an element from Group 1 of the Periodic Table. In another subembodiment, the reaction mixture is formed using a source of sodium (Na). Any M-containing compound which is not detrimental to the crystallization process is suitable. Sources for such Groups 1 and 2 elements include oxides, hydroxides, nitrates, sulfates, halogenides, oxalates, citrates and acetates thereof.

The SDA dication is typically associated with anions ($X^-$) which may be any anion that is not detrimental to the formation of the zeolite. Representative anions include elements from Group 17 of the Periodic Table (e.g., fluoride, chloride, bromide and iodide), hydroxide, acetate, sulfate, tetrafluoroborate, carboxylate, and the like.

The 1,5-bis(1-azonia-bicyclo[2.2.2]octane)pentane dication SDA of the present invention (represented by structure (1)) can be synthesized by reacting a dihaloalkane (such as 1,5-dibromopentane) with 1-azonia-bicyclo[2.2.2]octane. The 1,5-bis(1,4-diazabicyclo[2.2.2]octane)pentane dication SDA of the present invention (represented by structure (2)) can be synthesized by reacting a dihaloalkane (such as 1,5-dibromopentane) with 1,4-diazabicyclo[2.2.2]octane.

For each embodiment described herein, the molecular sieve reaction mixture can be supplied by more than one source. Also, two or more reaction components can be provided by one source.

The reaction mixture can be prepared either hatch wise or continuously. Crystal size, morphology and crystallization time of the molecular sieve described herein may vary with the nature of the reaction mixture and the synthesis conditions.

Crystallization and Post-Synthesis Treatment

In practice, the molecular sieve is prepared by:

(a) preparing a reaction mixture as described herein above; and (b) maintaining the reaction mixture under crystallization conditions sufficient to form the molecular sieve. (See, Harry Robson, *Verified Syntheses of Zeolitic Materials*, $2^{nd}$ revised edition, Elsevier, Amsterdam (2001)).

The reaction mixture is maintained at an elevated temperature until the molecular sieve is formed. The hydrothermal crystallization is usually conducted under pressure, and usually in an autoclave so that the reaction mixture is subject to autogenous pressure, at a temperature between 125° C. and 200° C.

The reaction mixture may be subjected to mild stirring or agitation during the crystallization step. It will be understood by a person skilled in the art that the molecular sieves described herein may contain impurities, such as amorphous materials, unit cells having framework topologies which do not coincide with the molecular sieve, and/or other impurities (e.g., organic hydrocarbons).

During the hydrothermal crystallization step, the molecular sieve crystals can be allowed to nucleate spontaneously from the reaction mixture. The use of crystals of the molecular sieve as seed material can be advantageous in decreasing the time necessary for complete crystallization to occur. In addition, seeding can lead to an increased purity of the product obtained by promoting the nucleation and/or formation of the molecular sieve over any undesired phases. When used as seeds, seed crystals are added in an amount between 1% and 10% of the weight of the source for silicon used in the reaction mixture.

Once the molecular sieve has formed, the solid product is separated from the reaction mixture by standard mechanical separation techniques such as filtration. The crystals are water-washed and then dried to obtain the as-synthesized molecular sieve crystals. The drying step can be performed at atmospheric pressure or under vacuum.

The molecular sieve can be used as-synthesized, but typically will be thermally treated (calcined). The term "as-synthesized" refers to the molecular sieve in its form after crystallization, prior to removal of the SDA cation. The SDA can be removed by thermal treatment (e.g., calcination), preferably in an oxidative atmosphere (e.g., air, gas with an oxygen partial pressure of greater than 0 kPa) at a temperature readily determinable by one skilled in the art sufficient to remove the SDA from the molecular sieve. The SDA can also be removed by photolysis techniques (e.g. exposing the SDA-containing molecular sieve product to light or electromagnetic radiation that has a wavelength shorter than visible light under conditions sufficient to selectively remove the organic compound from the molecular sieve) as described in U.S. Pat. No. 6,960,327 to Navrotsky and Parikh, issued Nov. 1, 2005.

The molecular sieve can subsequently be calcined in steam, air or inert gas at temperatures ranging from about 200° C. to about 800° C. for periods of time ranging from 1 to 48 hours, or more. Usually, it is desirable to remove the extra-framework cation (e.g. $Na^+$) by ion-exchange or other known method and replace it with hydrogen, ammonium, or any desired metal-ion.

Where the molecular sieve formed is an intermediate material, the target molecular sieve can be achieved using post-synthesis techniques to allow for the synthesis of a target material having a higher Si:Al ratio from an intermediate material by acid leaching or other similar dealumination methods.

The molecular sieve made from the process of the present invention can be formed into a wide variety of physical shapes. Generally speaking, the molecular sieve can be in the form of a powder, a granule, or a molded product, such as extradate having a particle size sufficient to pass through a 2-mesh (Tyler) screen and be retained on a 400-mesh (Tyler) screen. In cases where the catalyst is molded, such as by extrusion with an organic binder, the molecular sieve can be extruded before drying, or, dried or partially dried and then extruded.

The molecular sieve catalyst of the present invention can optionally be combined with one or more catalyst supports, active base metals, other molecular sieves, promoters, and mixtures thereof. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa.

Catalyst supports combinable with SSZ-81 include alumina, silica, zirconia, titanium oxide, magnesium oxide, thorium oxide, beryllium oxide, alumina-silica, amorphous alumina-silica, alumina-titanium oxide, alumina-magnesium oxide, silica-magnesium oxide, silica-zirconia, silica-thorium oxide, silica-beryllium oxide, silica-titanium oxide, titanium oxide-zirconia, silica-alumina-zirconia, silica-alumina-thorium oxide, silica-alumina-titanium oxide or silica-alumina-magnesium oxide, preferably alumina, silica-alumina, clays, and combinations thereof.

Exemplary active base or noble metals useful herein include those selected from the elements from Group 6 through Group 10 of the Periodic Table, their corresponding oxides and sulfides, and mixtures thereof. In one subembodiment, each base or noble metal is selected from the group consisting of nickel (Ni), palladium (Pd), platinum (Pt), cobalt (C iron (Fe), rhenium (Re), chromium (Cr), molybdenum (Mo), tungsten (W), and mixtures thereof. In another subembodiment, the hydroprocessing catalyst contains at least one Group 6 base metal and at least one base metal selected from Groups 8 through 10 of the periodic table. Exemplary metal combinations include Ni/Mo/W, Mi/Mo, Mo/W, Co/Mo, Co/W and W/Ni.

Promoters include those selected from phosphorous (P), boron (B), silicon (Si), aluminum (Al), and mixtures thereof.

SSZ-81 is useful in catalysts for a variety of hydrocarbon conversion reactions such as hydrocracking, fluidized catalytic cracking (FCC), hydroisomerization, dewaxing, olefin isomerization, alkylation of aromatic compounds and the like. SSZ-81 is also useful as an adsorbent for separations.

In one embodiment, SSZ-81 is used in a hydroisomerization process which includes the step of contacting SSZ-8, typically in the hydrogen form containing a noble metal such as platinum, palladium or a mixture thereof, with a feed containing $C_4$-$C_7$ linear and branched paraffins, under hydroisomerization conditions. In one particular subembodiment, a hydroisomerization process is provided which includes the step of contacting molecular sieve SSZ-81 based catalyst with a feed containing $C_4$-$C_7$ linear and branched paraffins, under hydroisomerization conditions sufficient to yield a liquid product having a higher research octane number (RON), as determined by ASTM D2699-09, than the feed.

The feed is typically a light straight run fraction, boiling within the range of 30° F. to 250° F. (−1° C. to 121° C.), for example from 60° F. to 200° F. (16° C. to 93° C.). The isomerization reaction is typically carried out in the presence of hydrogen. Hydrogen may be added to give a hydrogen-to-hydrocarbon ratio ($H_2$/HC) of between 0.5 and 10$H_2$/HC, for example between 1 and 8$H_2$/HC. Typically, the feed is contacted with SSZ-81 (or a catalyst containing SSZ-81) at a temperature in the range of from about 150° F. to about 700° F. (65.5° C. to 371° C.), at a pressure ranging from about 50 psig to about 2000 psig (0.345 MPa to 13.8 MPa), and a feed liquid hour space velocity (LHSV) ranging from about 0.5 to about 5 $h^{-1}$. See U.S. Pat. No. 4,910,006 and U.S. Pat. No. 5,316,753 for a flintier discussion of isomerization process conditions.

A low sulfur feed is useful in the present process. The feed desirably contains less than 10 ppm, for example less than 1 ppm or less than 0.1 ppm sulfur. In the case of a feed which is not already low in sulfur, acceptable levels can be reached by hydrogenating the feed in a presaturation zone with a hydrogenating catalyst which is resistant to sulfur poisoning. See the aforementioned U.S. Pat. No. 4,910,006 and U.S. Pat. No. 5,316,753 for a further discussion of this hydrodesulfurization process.

It is typical to limit the nitrogen level and the water content of the feed. Catalysts and processes which are suitable for these purposes are known to those skilled in the art.

After a period of operation, the catalyst can become deactivated by sulfur or coke. See the aforementioned U.S. Pat. No. 4,910,006 and U.S. Pat. No. 5,316,753 for a further discussion of methods of removing this sulfur and coke, and of regenerating the catalyst.

The conversion catalyst desirably contains one or more Group 8-10 metals. The Group 8-10 noble metals and their compounds, platinum, palladium, and iridium, or combinations thereof can be used. Rhenium and tin may also be used in conjunction with the noble metal. Typically, the metal is platinum or palladium. The amount of Group 8-10 metal present in the conversion catalyst should be within the normal range of use in hydroisomerizing catalysts, from about 0.05 to 2.0 weight percent, for example 0.2 to 0.8 weight percent.

Characterization of the Molecular Sieve

Molecular sieves made by the process of the present invention have a composition, as-synthesized and in the anhydrous state, as described in Table 2 (in terms of mole ratios), wherein compositional variables Q, A and M are as described herein above.

TABLE 2

|  | Broadest | Secondary |
|---|---|---|
| $SiO_2/Al_2O_3$ | 10-60 | 20-35 |
| (Q + A)/$SiO_2$ | 0.02-0.10 | 0.04-0.07 |
| M/$SiO_2$ | 0.01-1.0 | 0.02-0.04 |

Molecular sieves synthesized by the process of the present invention are characterized by their XRD pattern. The powder XRD pattern lines of Table 3 are representative of as-synthesized SSZ-81 made in accordance with this invention. Minor variations in the diffraction pattern can result from variations in the mole ratios of the framework species of the particular sample due to changes in lattice constants. In addition, sufficiently small crystals will affect the shape and intensity of peaks, leading to significant peak broadening. Minor variations in the diffraction pattern can also result from variations in the organic compound used in the preparation and from variations in the Si/Al mole ratio from sample to sample. Calcination can also cause minor shifts in the XRD pattern. Notwithstanding these minor perturbations, the basic crystal lattice structure remains unchanged.

TABLE 3

Characteristic Peaks for As-Synthesized SSZ-81

| 2 Theta[a] | d-spacing (Angstroms) | Relative Intensity (%)[b] |
|---|---|---|
| 7.02 | 12.58 | W |
| 7.41 | 11.91 | M |
| 7.41 peak-10.50[c] |  | W, broad band |
| 18.50-22.03 peak[d] |  | W, broad band |
| 22.03 | 4.03 | W-M |
| 22.58 | 3.94 | S |
| 23.30 | 3.81 | W |
| 24.12 | 3.69 | W |
| 25.10 | 3.55 | W |

TABLE 3-continued

Characteristic Peaks for As-Synthesized SSZ-81

| 2 Theta[a] | d-spacing (Angstroms) | Relative Intensity (%)[b] |
|---|---|---|
| 27.30 | 3.26 | W |
| 28.55 | 3.12 | W |

[a]±0.20
[b]The powder XRD patterns provided are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.
[c], [d]In the pattern for as-synthesized SSZ-81, it can be seen that there is a first low-intensity (W), broad-band running from the peak near 2θ = 7.4 degrees down to baseline at near 2θ = 10.5 degrees, and a second low-intensity, broad-band rising from the baseline at about 2θ = 18.5 degrees and then merging into a well-defined peak just beyond 22 degrees. This behavior is seen in all samples of as-synthesized SSZ-81.

The X-ray diffraction pattern lines of Table 4 are representative of calcined SSZ-81 made in accordance with this invention.

TABLE 4

Characteristic Peaks for Calcined SSZ-81

| 2 Theta[a] | d-spacing (Angstroms) | Relative Intensity (%)[b] |
|---|---|---|
| 7.45 | 11.86 | S |
| 7.45 peak-10.50[c] |  | W, broad band |
| 14.38 | 6.15 | W |
| 18.50-22.26 peak[d] |  | W, broad band |
| 22.26 | 3.99 | W |
| 22.79 | 3.90 | S |
| 23.53 | 3.78 | W-M |
| 24.36 | 3.65 | W-M |
| 25.37 | 3.51 | W |
| 26.37 | 3.38 | W |
| 27.53 | 3.24 | W |
| 28.67 | 3.11 | W |

[a]±0.20
[b]The powder XRD patterns provided are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.
[c], [d]In the pattern for as-synthesized 88Z-81, it can be seen that there is a first low-intensity (W), broad-band running from the peak near 2θ = 7.4 degrees down to baseline at near 2θ = 10.5 degrees, and a second low-intensity, broad-band rising from the baseline at about 2θ = 18.5 degrees and then merging into a well-defined peak just beyond 22 degrees. This behavior is seen in all samples of calcined SSZ-81.

The powder X-ray diffraction patterns presented herein were collected by standard techniques. The radiation was CuK-α radiation. The peak heights and the positions; as a function of 2θ where θ is the Bragg angle, were read from the relative intensities of the peaks (adjusting for background), and d, the interplanar spacing in Angstroms corresponding to the recorded lines, can be calculated.

EXAMPLES

The following examples demonstrate but do not limit the present invention.

Example 1

Synthesis of SSZ-81 Using 1,5-bis(1-azonia-bicyclo[2.2.2]octane)pentane Dication 5.0 g of a hydroxide solution of 1,5-bis(1-azonia-bicyclo [2.2.2]octane)pentane ([OH⁻]=0.4 mmol/g) was added to a Teflon container. Next, 0.18 g of zeolite Y-52 (as provided by Union Carbide Corp.), 1.50 g of a 1N NaOH solution and 0.50 g of water was added to the container. Finally, 0.50 g CAB-O-SIL M-5 fumed silica (Cabot Corporation) was slowly added and the gel was thoroughly mixed. The Teflon liner was then capped and sealed within a steel Parr autoclave. The autoclave was placed on a spit within a convection oven at 160° C. The autoclave was tumbled at 43 rpm over the course of 17 days in the heated oven. The autoclave was then removed and allowed to cool to room temperature. The solids were then recovered by filtration and washed thoroughly with deionized water. The solids were allowed to dry at room temperature.

The resulting product was analyzed by powder XRD. FIG. 1 shows the powder XRD pattern of the product of this Example. Table 5 below shows the powder X-ray diffraction lines for the resulting product.

TABLE 5

| 2 Theta[a] | d-spacing (Angstroms) | Relative Intensity (%) |
|---|---|---|
| 6.14 | 14.38 | 8.1 |
| 7.02 | 12.58 | 2.2 |
| 7.41 | 11.91 | 27.0 |
| 7.41 peak-10.50[b] |  | low-intensity, broad band |
| 18.50-22.03 peak[c] |  | low-intensity, broad band |
| 11.08 | 7.98 | 3.3 |
| 12.86 | 6.88 | 2.9 |
| 15.57 | 5.69 | 4.1 |
| 18.72 | 4.74 | 4.9 |
| 22.03 | 4.03 | 21.4 |
| 22.58 | 3.94 | 100.00 |
| 23.30 | 3.81 | 13.8 |
| 24.12 | 3.69 | 14.2 |
| 25.10 | 3.55 | 6.3 |
| 26.12 | 3.41 | 3.9 |
| 26.36 | 3.38 | 4.4 |
| 27.30 | 3.26 | 7.8 |
| 28.55 | 3.12 | 8.6 |
| 31.29 | 2.86 | 5.0 |
| 33.94 | 2.64 | 1.8 |
| 34.08 | 2.63 | 2.6 |
| 36.69 | 2.45 | 3.4 |

[a]±0.20
[b],[c]In the pattern for as-synthesized SSZ-81, it can be seen that there is a first low-intensity (W), broad-band running from the peak near 2θ = 7.4 degrees down to baseline at near 2θ = 10.5 degrees, and a second low-intensity, broad-band rising from the baseline at about 2θ = 18.5 degrees and then merging into a well-defined peak just beyond 22 degrees. This behavior is seen in all samples of as-synthesized SSZ-81.

Example 2

Calcination of SSZ-81

Figure 2:
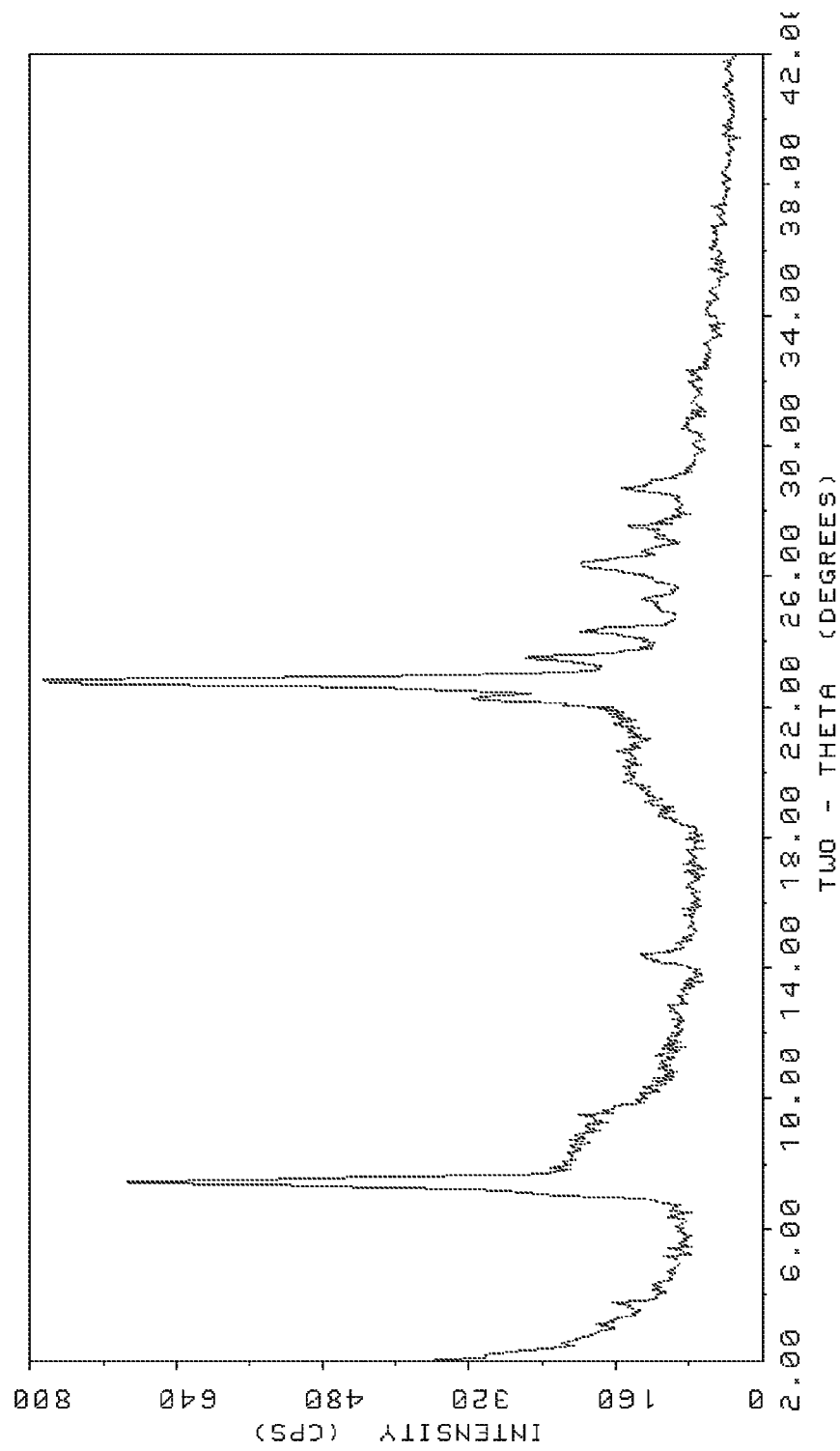
FIG. 2 shows the results of a scanning electron microscopy (SEM) analysis of the calcined molecular sieve of Example 2.

The product of Example 1 was calcined inside a muffle furnace under allow of 2% oxygen/98% nitrogen heated to 595° C. at a rate of 1° C./min and held at 595° C. for five hours, cooled and then analyzed by powder XRD. The resulting XRD pattern is shown in FIG. 2. Table 6 below shows the powder XRD lines for the calcined molecular sieve product.

TABLE 6

| 2 Theta[a] | d-spacing (Angstroms) | Relative Intensity (%) |
|---|---|---|
| 7.45 | 11.86 | 89.1 |
| 7.45 peak-10.50[b] |  | low-intensity, broad band |
| 9.85 | 8.97 | 7.5 |
| 11.62 | 7.61 | 6.7 |
| 14.38 | 6.15 | 7.3 |
| 18.50-22.26 peak[c] |  | low-intensity, broad band |
| 22.26 | 3.99 | 15.5 |
| 22.79 | 3.90 | 100.00 |
| 23.53 | 3.78 | 21.9 |
| 24.36 | 3.65 | 19.4 |

TABLE 6-continued

| 2 Theta[a] | d-spacing (Angstroms) | Relative Intensity (%) |
|---|---|---|
| 25.37 | 3.51 | 7.6 |
| 26.37 | 3.38 | 13.3 |
| 26.69 | 3.34 | 5.5 |
| 27.53 | 3.24 | 10.4 |
| 28.67 | 3.11 | 6.1 |

[a]±0.20
[b],[c]In the pattern for calcined SSZ-81, it can be seen that there is a first low-intensity (W), broad-band running from the peak near 2θ = 7.4 degrees down to baseline at near 2θ = 10.5 degrees, and a second low-intensity, broad-band rising from the baseline at about 2θ = 18.5 degrees and then merging into a well-defined peak just beyond 22 degrees. This behavior is seen in all samples of calcined SSZ-81.

The XRD pattern indicates that the material remains stable after calcination to remove the organic SDA.

Example 3

$NH_4^+$ Exchange

Ion-exchange of calcined SSZ-81 material (prepared in Example 2) is performed using $NH_4NO_3$ to convert the molecular sieve from its $Na^+$ form to the $NH_4^+$ form, and, ultimately, the $H^+$ form. Typically, the same mass of $NH_4NO_3$ as the molecular sieve is slurried in water at a ratio of 25-50:1 water to zeolite. The exchange solution is heated at 95° C. for 2 hours and then filtered. This procedure can be repeated up to three times. Following the final exchange, the molecular sieve is washed several times with water and dried. This $NH_4^+$ form of SSZ-81 can then be converted to the $H^+$ form by calcination (as described in Example 2) to 540'C.

Example 4

Constraint Index 0.5 grams of calcined $H^+$ form material prepared per Example 3, in a 20-40 pelletized and meshed range, was loaded into a stainless steel reactor (glass wool packing on both sides of the catalyst bed) and run in a Constraint Index test (50% n-hexane/50% 3-methylpentane (3-MP)), A normal feed rate was used (8 µl/min.) and a first test was run at 260° C. (500° F.) and a second test was run at 316° C. (600° F.). Each test was ran after the catalyst had been dried in the reactor to near 538° C. (1000° F.). Helium flow was used. (See, Zones and Harris, Microporous and Mesoporous Materials 35-36 (2000), pp, 31-46.)

As shown in Tables 7 and 8, at 10 minutes on-stream, ~92% of the feed was being converted with approximately equal amounts of each reactant in the first test, and in the second test over 99% of the feed was being converted with about equal amounts of each reactant.

TABLE 7

| n-$C_6$ conversion (%) | 89.7 |
|---|---|
| 3-methylpentane conversion (%) | 95.1 |
| Feed conversion (%) | 92.4 |
| Constraint Index (including 2-MP) | 1.05 |
| Constraint Index (excluding 2-MP) | 0.75 |

MP = methylpentane

TABLE 8

| n-$C_6$ conversion (%) | 99.3 |
|---|---|
| 3-MP (%) | 99.2 |
| Feed conversion (%) | 99.3 |

TABLE 8-continued

| | |
|---|---|
| Constraint Index (including 2-MP) | 1.21 |
| Constraint Index (excluding 2-MP) | 1.03 |

MP = methylpentane

Example 5

Adsorption of 2,2-Dimethylbutane

The calcined material of Example 3 was then tested for the uptake of the hydrocarbon 2,2-dimethylbutane. This adsorbate does not enter small pore zeolites (8-ring portals) and sometimes is hindered in entering intermediate pore zeolites like ZSM-5. The SSZ-81 showed a profile characteristic of a multi-dimensional, large-pore material (such as Y zeolite), showing rapid uptake and high pore filling.

At P/Po of ~0.3 and at room temperature, SSZ-81 was shown to adsorb over 0.18 cc/gram after 15 minutes of exposure to the 2,2-dimethylbutane adsorbate, and about 0.19 cc/gram after about 1 hour of exposure to the adsorbate.

Example 6

Synthesis of SSZ-81 Using a Combination of Dications 1.25 g of a hydroxide solution of 1,5-bis(1-azonia-bicyclo[2.2.2]octane)pentane ([OH$^-$]=0.40 mmol/g) and 3.75 g of a hydroxide solution of 1,5-bis(1,4-diazabicyclo[2.2.2]octane)pentane ([OH$^-$]=0.41 mmol/g) were added to a Teflon container. Next, 0.18 g of zeolite Y-52 (provided by Union Carbide Corporation), 1.50 g of a 1N NaOH solution and 0.50 g of water were added to the container. Finally, 0.50 g CAB-O-SIL M-5 fumed silica (Cabot Corporation) was slowly added and the gel was thoroughly mixed. The Teflon liner was then capped and sealed within a steel Parr autoclave. The autoclave was placed on a spit within a convection oven at 160° C. The autoclave was tumbled at 43 rpm over the course of four weeks in the heated oven. The autoclave was then removed and allowed to cool to room temperature. The solids were then recovered by filtration and washed thoroughly with deionized water. The solids were allowed to dry at room temperature.

The resulting product was analyzed by powder XRD. The XRD analysis indicated the product was SSZ-81.

Example 7

Synthesis of SSZ-81 Using a 1,5-bis(1,4-diazabicyclo[2.2.2]octane)pentane Dication 5.0 g of a hydroxide solution of 1,5-bis(1,4-diazabicyclo[2.2.2]octane)pentane ([OH$^-$]=0.41 mmol/g) was added to a Teflon container. Next, 0.18 g of zeolite Y-52 (provided by Union Carbide Corp), 1.50 g of a 1N NaOH solution and 0.50 g of water were added to the container. Finally, 0.50 g CAB-O-SIL M-5 fumed silica (Cabot Corporation) was slowly added and the gel was thoroughly mixed. The Teflon liner was then capped and sealed within a steel Parr autoclave. The autoclave was placed on a spit within a convection oven at 160° C. The autoclave was tumbled at 43 rpm over the course of six weeks in the heated oven, with periodic interruption to look for product formation. The autoclave was then removed after 6 weeks and allowed to cool to room temperature. The solids were then recovered by filtration and washed thoroughly with deionized water. The solids were allowed to dry at room temperature.

The resulting product was analyzed by powder XRD. The XRD analysis indicated the product was a mixture of SSZ-81 and some remaining unreacted zeolite Y-52.

Example 8

Preparation of Hydroisomerization Catalyst

Al-SSZ-81 in H$^+$-form prepared in accordance with the procedure outlined in Example 3 herein, was ion-exchanged with an aqueous (NH$_3$)$_4$Pd(NO$_3$)$_2$ solution at pH of ~10.3 to load the zeolite with 0.5 wt % Pd. The Pd/Al-SSZ-81 molecular sieve was then calcined in air at 45017 (232° C.) for 5 hours, and subsequently reduced in hydrogen prior to the catalytic experiment set forth in Example 9.

Example 9 n-Hexane Hydroisomerization over Pd/Al-SSZ-81

The catalytic reaction of hydroisomerization n-hexane was carried out using the Pd/SSZ-81 catalyst prepared in Example 8 herein, in a flow-type fixed bed reactor with pure n-hexane as the feed. The hydroisomerization conditions included a pressure of 200 pounds per square inch gauge (psig)(1.38 MPa), a liquid hour space velocity (LHSV) of 1 h$^{-1}$, and a H$_2$ to hydrocarbon molar ratio of 6:1. The reaction temperatures ranged from 400 to 620° F. (204-327° C.) in 10° F. (5.5° C.) increments. The reaction products were analyzed with an on-line gas chromatograph to quantify all the cracking and isomerization products. Representative results are shown in Table 9.

TABLE 9

| | Temperature | 500° F. (260° C.) | 520° F. (271° C.) |
|---|---|---|---|
| | n-Hexane conversion (mol %) | 18.99 | 80.84 |
| | Cracking yield (mol %) | 0.03 | 1.28 |
| | Isomerization yield (mol %) | 18.96 | 79.56 |
| Distribution of branched C$_6$ paraffin isomers (mol %) | 2,2-dimethyl-butane | 0.64 | 11.90 |
| | 2,3-dimethyl-butane | 5.26 | 12.45 |
| | 2-methyl-pentane | 58.22 | 45.94 |
| | 3-methyl-pentane | 35.88 | 29.71 |
| | Total | 100.0 | 100.0 |

What is claimed is:

1. A process comprising contacting molecular sieve SSZ-81 with a feed containing C$_4$-C$_7$ linear and branched paraffins under hydroisomerization conditions.

2. The process according to claim 1, wherein the hydroisomerization process yields a liquid product having a higher research octane number (RON), as determined by ASTM D2699-09, than the feed.

3. The process according to claim 1, wherein the molecular sieve has a composition, in the as-synthesized and anhydrous state, in terms of mole ratios, as follows:

| | |
|---|---|
| SiO$_2$/Al$_2$O$_3$ | 10-60 |
| (Q + A)/SiO$_2$ | 0.02-0.10 |
| M/SiO$_2$ | 0.01-1.0 | wherein:
(1) M is selected from the group consisting of elements from Groups 1 and 2 of the Periodic Table;
(2) Q is at least one 1,5-bis(1-azonia-bicyclo[2.2.2]octane) pentane dication structure directing agent, and Q≥0; and
(3) A is at least one 1,5-bis(1,4-diazabicyclo[2.2.2]octane pentane dication structure directing agent, and A≥0.

4. The process according to claim 1, wherein the molecular sieve has a composition, in the as-synthesized and anhydrous state, in terms of mole ratios, as follows:

| | |
|---|---|
| $SiO_2/Al_2O_3$ | 20-35 |
| $(Q + A)/SiO_2$ | 0.04-0.07 |
| $M/SiO_2$ | 0.02-0.04 | wherein:
(1) M is selected from the group consisting of elements from Groups 1 and 2 of the Periodic Table;
(2) Q is at least one 1,5-bis(1-azonia-bicyclo[2.2.2]octane) pentane dication structure directing agent, and Q≥0; and
(3) A is at least one 1,5-bis(1,4-diazabicyclo[2.2.2]octane) pentane dication structure directing agent, and A≥0.

5. The process according to claim 1, wherein the hydroisomerization conditions sufficient to yield, a liquid product having a higher research octane number (RON), as determined by ASTM D2699-09, than the feed.

6. The process according to claim 1, wherein the feed is a light straight run fraction, boiling within the range of 30° F. to 250° F. (−1° C. to 121° C.).

7. The process according to claim 1, wherein the feed is contacted with SSZ-81 at a temperature between 150° F. and 700° F. (65.5° C. to 371° C.), at a pressure between 50 psig and 2000 psig (0.345 MPa to 13.8 MPa), and a feed liquid hour space velocity between 0.5 and 5 $h^{-1}$.

* * * * *